(12) United States Patent
Park et al.

(10) Patent No.: US 11,647,943 B2
(45) Date of Patent: May 16, 2023

(54) PH MEASURING DEVICE AND PH MONITORING SYSTEM INCLUDING SAME

(71) Applicant: Samsung Medical Center, Seoul (KR)

(72) Inventors: Jung Ho Park, Seoul (KR); Eung Bo Kim, Daejeon (KR)

(73) Assignee: SAMSUNG MEDICAL CENTER, Seoul (KR)

( * ) Notice: Subject to any disclaimer, the term of this patent is extended or adjusted under 35 U.S.C. 154(b) by 301 days.

(21) Appl. No.: 16/615,497

(22) PCT Filed: Jun. 5, 2018

(86) PCT No.: PCT/KR2018/006384
§ 371 (c)(1),
(2) Date: Nov. 21, 2019

(87) PCT Pub. No.: WO2018/226003
PCT Pub. Date: Dec. 13, 2018

(65) Prior Publication Data
US 2020/0085364 A1    Mar. 19, 2020

(30) Foreign Application Priority Data
Jun. 7, 2017 (KR) .................. 10-2017-0070963

(51) Int. Cl.
*A61B 5/1473* (2006.01)
*A61B 5/00* (2006.01)
(Continued)

(52) U.S. Cl.
CPC ............ *A61B 5/4211* (2013.01); *A61B 5/002* (2013.01); *A61B 5/1473* (2013.01);
(Continued)

(58) Field of Classification Search
CPC ... A61B 5/145; A61B 5/14539; A61B 5/4233; G01N 27/4167
See application file for complete search history.

(56) References Cited

U.S. PATENT DOCUMENTS 6,689,056 B1 * 2/2004 Kilcoyne ............. A61B 5/4211
600/300
8,257,257 B2    9/2012 Takizawa et al.
(Continued)

FOREIGN PATENT DOCUMENTS

CN    201275065 Y    7/2009
CN    103002840 A    3/2013
(Continued)

OTHER PUBLICATIONS

OA issued in KR patent application No. 10-2017-0070963, dated Dec. 11, 2018.
(Continued)

*Primary Examiner* — Puya Agahi
*Assistant Examiner* — Grace L Rozanski
(74) *Attorney, Agent, or Firm* — Knobbe, Martens, Olson & Bear LLP

(57) ABSTRACT

A pH measuring device is disclosed. One aspect includes a body unit including a hollow portion and a through-portion formed in a first region so that the hollow portion communicates with the outside; an electrode unit including a reference electrode and a sensing electrode including different materials and configured to measure the pH in a living body by allowing a first end to be located in the hollow portion and a second end opposite to the first end to be exposed to the outside of the body unit through the through-portion; and a wireless communication unit configured to transmit a pH measurement value sensed by the electrode unit to the outside.

8 Claims, 6 Drawing Sheets

(51) Int. Cl.
  *A61B 5/145* (2006.01)
  *G01N 27/30* (2006.01)
  *G01N 27/416* (2006.01)
(52) U.S. Cl.
  CPC ........ *A61B 5/14539* (2013.01); *A61B 5/4233* (2013.01); *G01N 27/301* (2013.01); *G01N 27/302* (2013.01); *G01N 27/4167* (2013.01)

(56) References Cited

U.S. PATENT DOCUMENTS

| | | | | |
|---|---|---|---|---|
| 2002/0123748 | A1* | 9/2002 | Edwards | A61B 18/1477 606/41 |
| 2004/0193029 | A1* | 9/2004 | Glukhovsky | A61B 5/076 128/903 |
| 2011/0046479 | A1* | 2/2011 | Imran | A61B 5/6801 604/890.1 |
| 2016/0249840 | A1* | 9/2016 | Pesantez | A61B 5/14865 205/778 |
| 2016/0317729 | A1* | 11/2016 | Criscione | A61N 1/39622 |
| 2018/0368745 | A1* | 12/2018 | Sufi | A61B 5/14507 |
| 2019/0254608 | A1* | 8/2019 | Jiang | A61B 5/14539 |

FOREIGN PATENT DOCUMENTS

| | | |
|---|---|---|
| CN | 103852508 A | 6/2014 |
| CN | 105510388 A | 4/2016 |
| CN | 105823811 A | 8/2016 |
| CN | 205656161 U | 10/2016 |
| CN | 106452649 A | 2/2017 |
| CN | 106645297 A | 5/2017 |
| KR | 10-0399572 B1 | 9/2003 |
| KR | 10-1048916 B1 | 7/2011 |
| KR | 10-1566796 B1 | 11/2015 |
| WO | WO 2012/007048 A1 | 1/2012 |

OTHER PUBLICATIONS

Notice of Allowance issued in KR patent application No. 10-2017-0070963, dated Jun. 19, 2019.
First Office Action dated Oct. 11, 2021 in corresponding Chinese Patent Application No. 201880036966.7, 8 pp.
Office Action issued in corresponding Chinese Patent Application No. 201880036966.7, dated Jul. 4, 2022.

* cited by examiner

PH MEASURING DEVICE AND PH MONITORING SYSTEM INCLUDING SAME

This application is the U.S. National Phase under 35 U.S.C. § 371 of International Application PCT/KR2018/006384, filed Jun. 5, 2018, designating the U.S., and published in Korean as WO 2018/226003 on Dec. 13, 2018, which claims priority to Korean Patent Application No. 10-2017-0070963, filed Jun. 7, 2017, the entire contents of which are incorporated herein by reference.

TECHNICAL FIELD

Embodiments of the present disclosure relate to a pH measuring device for diagnosing gastroesophageal reflux disease and a pH monitoring system including the pH measuring device.

BACKGROUND ART

Although gastroesophageal reflux disease is recognized as a common health problem of Western societies such as the United States, the prevalence of gastroesophageal reflux disease has increased even in Korea due to factors such as a change in lifestyles and dietary habits and stress. In order to diagnose gastroesophageal reflux disease, the acidity (pH) in the esophagus is generally measured, and an endoscopic method or a method of measuring pH in the esophagus by wire or wirelessly has been proposed.

An endoscopic method that checks the degree of damage to esophageal tissue caused by the reflux of gastric acid involves diagnosing gastroesophageal reflux disease through inflammation occurring at the gastroesophageal junction. However, because more than half of patients with gastroesophageal reflux disease show normal results with no visible inflammation, the endoscopic method has a problem with reliability and accuracy. A method of measuring pH in the esophagus that is performed to evaluate patients who do not respond to medication or show atypical symptoms and determine the degree of normal acid exposure before a procedure involves inserting a catheter having an acid measuring function through a nasal cavity, placing the catheter on a lower esophageal sphincter, and maintaining the catheter for 24 hours. An examinee always carries a separate measuring unit connected to an inserted measuring device and, when he/she feels a symptom such as reflux, he/she records the symptom, and after 24 hours, a diagnosis is made through separate analysis. However, when the method of measuring pH in the esophagus is performed by wire, because the inserted catheter may cause pain, ache, and discomfort in the nasal cavity and pharynx and there is a limitation in measurement during a daily activity such as eating or exercising, the accuracy of the method is reduced. Also, because the wired method is performed for 24 hours but symptoms may not appear within the 24 hours sometimes, there is a limitation in measurement.

DESCRIPTION OF EMBODIMENTS

Technical Problem

In order to solve such problems, objectives of embodiments of the present disclosure are to provide a pH measuring device capable of transmitting a pH value that is wirelessly measured to the outside while being inserted into an esophageal wall, and a pH monitoring system including the pH measuring device.

Solution to Problem

An embodiment of the present disclosure provides a pH measuring device including: a body unit including a hollow portion therein and a through-portion formed in a first region so that the hollow portion communicates with the outside; an electrode unit including a reference electrode and a sensing electrode including different materials and configured to measure the pH in a living body by allowing a first end to be located in the hollow portion and a second end opposite to the first end to be exposed to the outside of the body unit through the through-portion; and a wireless communication unit configured to transmit a pH measurement value sensed by the electrode unit to the outside.

Advantageous Effects of Disclosure

A pH measuring device and a pH monitoring system including the same according to embodiments of the present disclosure may transmit a pH measurement value wirelessly to the outside while being inserted into the esophagus to minimize a user's pain, obtain a stable pH measurement value, and thus improve the accuracy of diagnosing gastroesophageal reflux disease.

BEST MODE

Figure 1:
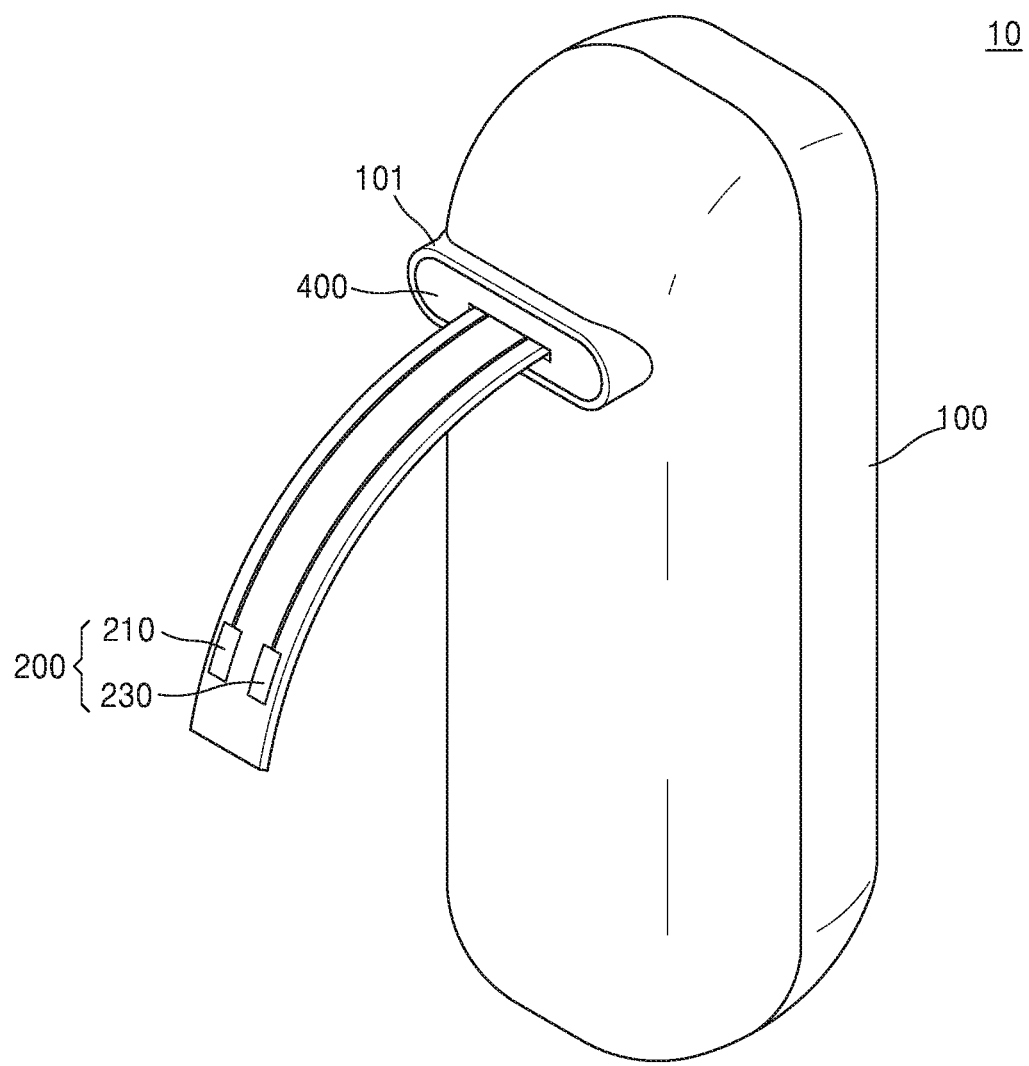
FIG. 1 is a conceptual view illustrating a pH measuring device according to an embodiment of the present disclosure.

An embodiment of the present disclosure provides a pH measuring device including: a body unit including a hollow portion therein and a through-portion formed in a first region so that the hollow portion communicates with the outside; an electrode unit including a reference electrode and a sensing electrode including different materials and configured to measure the pH in a living body by allowing a first end to be located in the hollow portion and a second end opposite to the first end to be exposed to the outside of the body unit through the through-portion; and a wireless communication unit configured to transmit a pH measurement value sensed by the electrode unit to the outside.

The reference electrode may be a silver/silver chloride (Ag/AgCl) electrode, and the sensing electrode may be formed of a metal oxide including one from among iridium/iridium oxide (Ir/IrOx), tin oxide ($SnO_2$), platinum oxide ($PtO_2$), titanium dioxide ($TiO_2$), osmium dioxide ($OsO_2$), rhodium dioxide ($RhO_2$), ruthenium oxide ($RuO_2$), and tantalum pentoxide ($Ta_2O_5$).

The wireless communication unit may be electrically connected to the electrode unit and may be further configured to transmit the sensed pH measurement value to the outside by using a resonant circuit including an inductor and a capacitor.

The body unit may be formed of at least one material from among ceramic, polymer, and plastic.

The pH measuring device may further include a sealing member configured to seal the through-portion in a state where the second end of the electrode unit is exposed to the outside.

A concave groove that is concave inward from a surface of the body unit may be formed in a second region spaced apart by a predetermined interval from the first region of the body unit.

An embodiment of the present disclosure provides a pH monitoring system including: a pH measuring device including a body unit including a hollow portion therein and a through-portion formed in a first region so that the hollow portion communicates with the outside, an electrode unit including a reference electrode and a sensing electrode including different materials and configured to measure the pH in a living body by allowing a first end of the electrode unit to be located in the hollow portion and a second end opposite to the first end to be exposed to the outside of the body unit through the through-portion, and a wireless communication unit configured to transmit a pH measurement value sensed by the electrode unit to the outside; and a reader configured to receive the pH measurement value transmitted from the wireless communication unit of the pH measuring device.

The wireless communication unit may be electrically connected to the electrode unit and may be further configured to transmit the sensed pH measurement value to the outside through a resonant frequency by using a resonant circuit including an inductor and a capacitor.

The reference electrode may be a silver/silver chloride (Ag/AgCl) electrode, and the sensing electrode may be formed of a metal oxide including one from among iridium/iridium oxide (Ir/IrOx), tin oxide ($SnO_2$), platinum oxide ($PtO_2$), titanium dioxide ($TiO_2$), osmium dioxide ($OsO_2$), rhodium dioxide ($RhO_2$), ruthenium oxide ($RuO_2$), and tantalum pentoxide ($Ta_2O_5$).

A concave groove that is concave inward from a surface of the body unit may be formed in a second region spaced apart by a predetermined interval from the first region of the body unit.

Other features and advantages of the present disclosure will become more apparent from the drawings, the claims, and the detailed description.

MODE OF DISCLOSURE

The present disclosure may include various embodiments and modifications, and exemplary embodiments thereof will be illustrated in the drawings and will be described herein in detail. The effects and features of the present disclosure and the accompanying methods thereof will become apparent from the following description of the embodiments, taken in conjunction with the accompanying drawings. However, the present disclosure is not limited to the embodiments described below, and may be embodied in various modes.

The present disclosure will now be described more fully with reference to the accompanying drawings, in which embodiments of the present disclosure are shown, and in the drawings, the same elements are denoted by the same reference numerals and a repeated explanation thereof will not be given.

It will be understood that although the terms "first", "second", etc. may be used herein to describe various elements, these elements should not be limited by these terms and these terms are only used to distinguish one element from another.

As used herein, the singular forms "a", "an", and "the" are intended to include the plural forms as well, unless the context clearly indicates otherwise.

It will be further understood that the terms "comprises" and/or "comprising" used herein specify the presence of stated features or components, but do not preclude the presence or addition of one or more other features or components.

It will be understood that when a layer, region, or element is referred to as being "on" another layer, region, or element, it may be directly on the other layer, region, or element or may be indirectly on the other layer, region, or element with intervening layers, regions, or elements therebetween.

In the drawings, sizes of elements may be exaggerated for convenience of explanation. In other words, because sizes and thicknesses of elements in the drawings are arbitrarily illustrated for convenience of explanation, the following embodiments are not limited thereto.

When a certain embodiment may be implemented differently, a specific process order may be different from the described order. For example, two consecutively described processes may be performed substantially at the same time or performed in an order opposite to the described order.

It will be understood that when a layer, region, or element is referred to as being "connected", the layer, region, or element may be directly connected or may be indirectly connected with intervening layers, regions, or elements therebetween. For example, when a layer, region, or element is electrically connected, the layer, region, or element may be directly electrically connected or may be indirectly electrically connected with intervening layers, regions, or elements therebetween.

Figure 2:
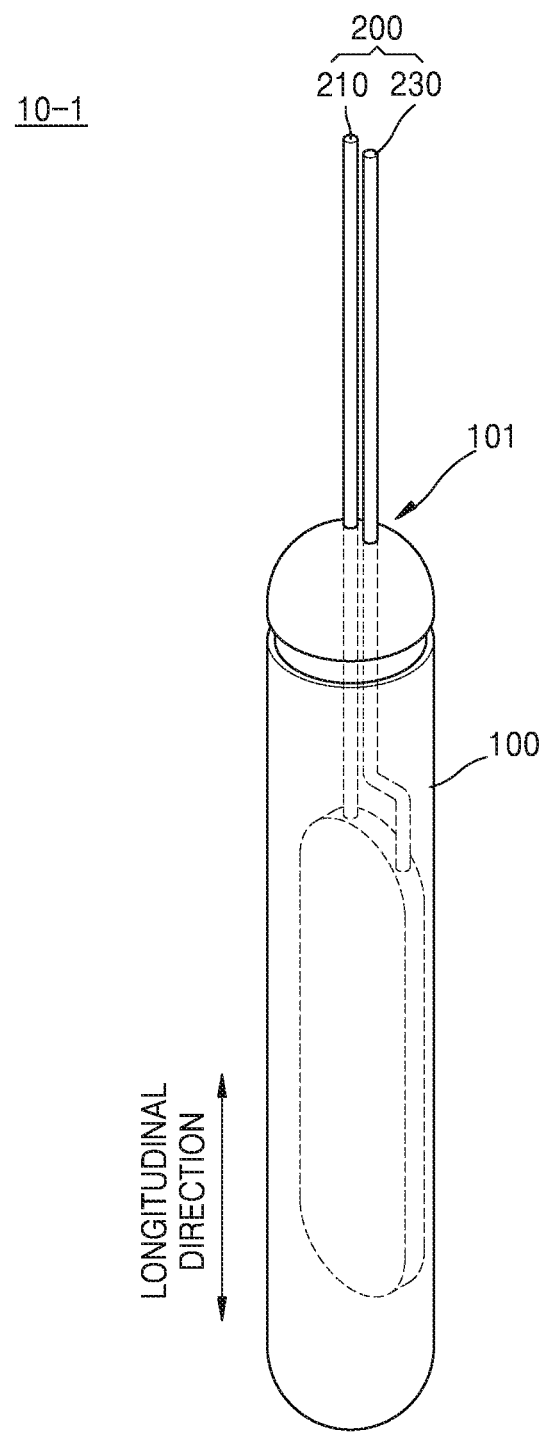
FIG. 2 is a conceptual view illustrating another embodiment of FIG. 1.
Figure 3:
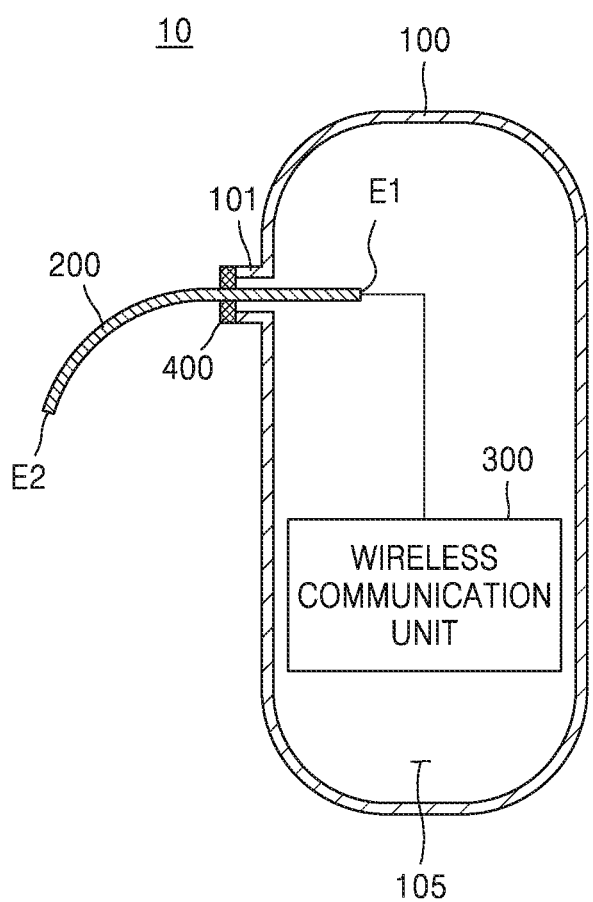
FIG. 3 is a cross-sectional view of a pH measuring device of FIG. 1.
Figure 4:
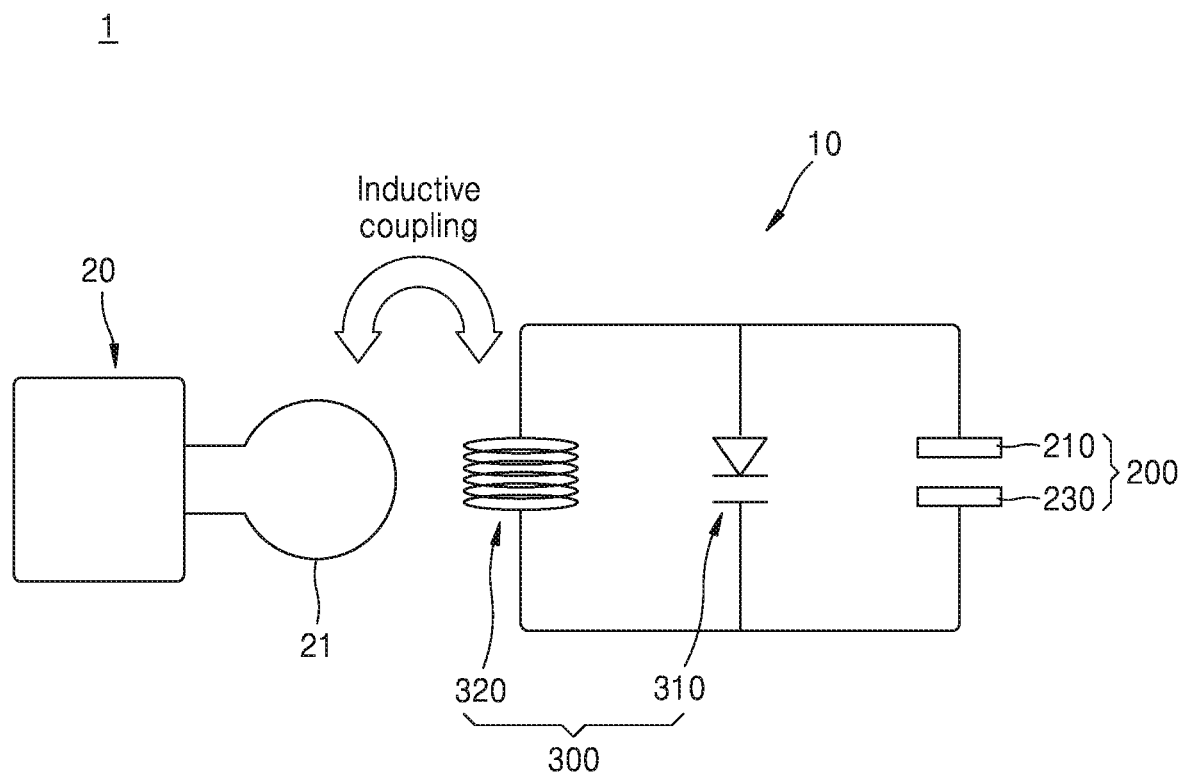
FIG. 4 is a circuit diagram illustrating a circuit configuration of a pH monitoring system of FIG. 1.

FIG. 1 is a conceptual view illustrating a pH measuring device according to an embodiment of the present disclosure, FIG. 2 is a conceptual view illustrating another embodiment of FIG. 1, and FIG. 3 is a cross-sectional view of the pH measuring device of FIG. 1. FIG. 4 is a circuit diagram illustrating a circuit configuration of a pH monitoring system of FIG. 1.

Referring to FIGS. 1 through 4, a pH monitoring system 1 according to an embodiment of the present disclosure may include a pH measuring device 10 and a reader 20.

The pH measuring device 10 may be inserted into an esophageal wall of an examinee and may transmit a pH measurement value measured by using an electrode unit, which protrudes outward beyond the esophageal wall, to the outside. In detail, the pH measuring device 10 may include a body unit 100, an electrode unit 200, and a wireless communication unit 300. Also, the pH measuring device 10 may further include a sealing member 400 for sealing the body unit 100.

The body unit 100 may include a hollow portion 105 therein and a through-portion 101 formed in a first region so that the hollow portion 105 communicates with the outside. Corners of the body unit 100 may be round to minimize the examinee's discomfort when the body unit 100 is inserted into the esophageal wall. Also, the body unit 100 may be formed of a harmless material even when the body unit 100 is inserted into a living body. For example, the body unit 100 may be formed of a material such as ceramic, polymer, plastic, or silicon. Alternatively, the body unit 100 may be formed of a flexible material harmless to a human body, for example, a fluorine resin such as polytetrafluoroethylene (PTEE) that is known as Teflon, hexafluoropropylene (FEP), or perfluoroalkyl vinyl ether (PFA), polyethylene, polystyrene, polyester, polyimide, polyamide, or polyurethane.

The through-portion 101 may be formed in the first region of the body unit 100, and the electrode unit 200 electrically connected to an internal circuit through the through-portion 101 may be exposed to the outside. Although the through-portion 101 is formed in the first region where the electrode unit 200 is exposed in a direction different from a longitudinal direction of the body unit 100, the present disclosure is not limited thereto. Referring to FIG. 2, in another embodiment, the through-portion 101 may be formed at a side of the body unit 100 to expose the electrode unit 200 to the outside in the longitudinal direction of the body unit 100. As shown in FIG. 2, because the pH measuring device 10 in which the electrode unit 200 is exposed to the outside through the through-portion 101 in the longitudinal direction of the body unit 100 may have a slim structure, the pH measuring device 10 may be stably mounted on submucosal tissue. In this case, the electrode unit 200 may be manufactured as a wire, and accordingly, the electrode unit 200 may be easily inserted by using an endoscope side channel.

The electrode unit 200 may include a first end E1 located in the hollow portion 105 and a second end E2 located opposite to the first end E1 and exposed to the outside of the body unit 100 through the through-portion 101, and may measure acidity, i.e., pH, in the living body. The electrode unit 200 may include a reference electrode 210 and a sensing electrode 230 including different materials. The reference electrode 210 may provide a potential ideally independent of pH, and the sensing electrode 230 may provide a potential dependent on pH in the living body, specifically, the esophagus. A potential difference between the reference electrode 210 and the sensing electrode 230 may be derived from Equation 1.

$$V_{pH} = V_0 - \frac{RT}{nF}\text{pH} \quad \text{[Equation 1]}$$

T is a temperature value K, $V_o$ is a voltage V of the reference electrode 210, and $V_{pH}$ is a voltage V of the sensing electrode 230. F is a Faraday constant, n is the number of moles of electrons transferred in an electrochemical cell reaction, and R is an ideal gas constant (8.3144 J. $K^{-1}$. $mol^{-1}$) In other words, the electrode unit 200 may measure the potential $V_o$ of the reference electrode 210 and the potential $V_{pH}$ of the sensing electrode 230, and may measure the pH in the living body that is proportional to a potential difference.

Because each of the reference electrode 210 and the sensing electrode 230 has to be implemented in a size not affected by the peristalsis of the esophagus when the pH measuring device 10 is inserted into the esophagus, each of the reference electrode 210 and the sensing electrode 230 may be manufactured as a micro-electrode by using a wire method or a microelectromechanical systems (MEMS) method. In this case, the reference electrode 210 and the sensing electrode 230 may include different materials.

The reference electrode 210 may be a metal wire including silver/silver chloride (Ag/AgCl), and the sensing electrode 230 may be formed of a metal oxide including iridium/iridium oxide (Ir/IrOx) having the advantages of continuous detection, easy preparation, and fast and stable reactions to various materials. However, the present disclosure is not limited thereto, and the sensing electrode 230 may be formed of a metal oxide including one selected from among tin oxide ($SnO_2$), platinum oxide ($PtO_2$), titanium dioxide ($TiO_2$), osmium dioxide ($OsO_2$), rhodium dioxide ($RhO_2$), ruthenium oxide ($RuO_2$), and tantalum pentoxide ($Ta_2O_5$). When the sensing electrode 230 is formed of a metal oxide including Ir/IrOx, the sensing electrode 230 may be manufactured by using a direct oxidation method. For example, the sensing electrode 230 may be manufactured by soaking an iridium (Ir) wire in a 6 M HCL solution, performing ultrasonic cleaning by using deionized water, wetting a surface with a 1 M NaOH solution, and performing oxidization at 800° C. for 4 minutes in an electric oven.

The wireless communication unit 300 may transmit a pH measurement value in the esophagus sensed by the electrode unit 200 to the outside. Although the wireless communication unit 300 may use any method as long as the wireless communication unit 300 may wirelessly transmit the pH measurement value to the outside, the present disclosure will be described on the assumption that the pH measurement value is transmitted to the outside by using a resonant circuit. The wireless communication unit 300 may be electrically connected to the electrode unit 200 and may transmit the sensed pH measurement value to the outside by using the resonant circuit including an inductor 320 and a capacitor 310. The resonant circuit including the inductor 320 and the capacitor 310 may produce a resonant frequency due to a potential difference of the electrode unit 200 electrically connected to the resonant circuit. In this case, when the capacitor 310 is a varactor in the present disclosure, a resonant frequency may be changed by changing a capacitor value by using a potential difference occurring according to a pH concentration.

The reader 20 located outside the examinee may detect the resonant frequency and may provide a pH measurement value according to the resonant frequency to the examinee or an examiner. The reader 20 may include a sensing coil 21 capable of sensing the resonant frequency through inductive coupling. Also, the reader 20 may further include a database (not shown) capable of storing the pH measurement value measured at predetermined intervals. By using the pH measurement value stored in the database (not shown) at predetermined intervals for a certain period of time, the reader 20 may diagnose whether the examinee has reflux.

Because the pH measuring device 10 is inserted into the living body, in order to prevent a harmful substance from being discharged from the inside of the pH measuring device 10 to the outside or the pH measuring device 10 from being corroded due to body fluids in the living body, the body unit 100 has to be sealed. In this case, the through-portion 101 of the body unit 100 through which the electrode unit 200 passes may have an open portion, and in order to seal the open portion, the pH measuring device 10 may further include the sealing member 400. The sealing member 400 may seal the through-portion 101 in a state where the second end E2 of the electrode unit 200 is exposed to the outside and may be formed of a material harmless to the human body such as silicon.

Figure 5:
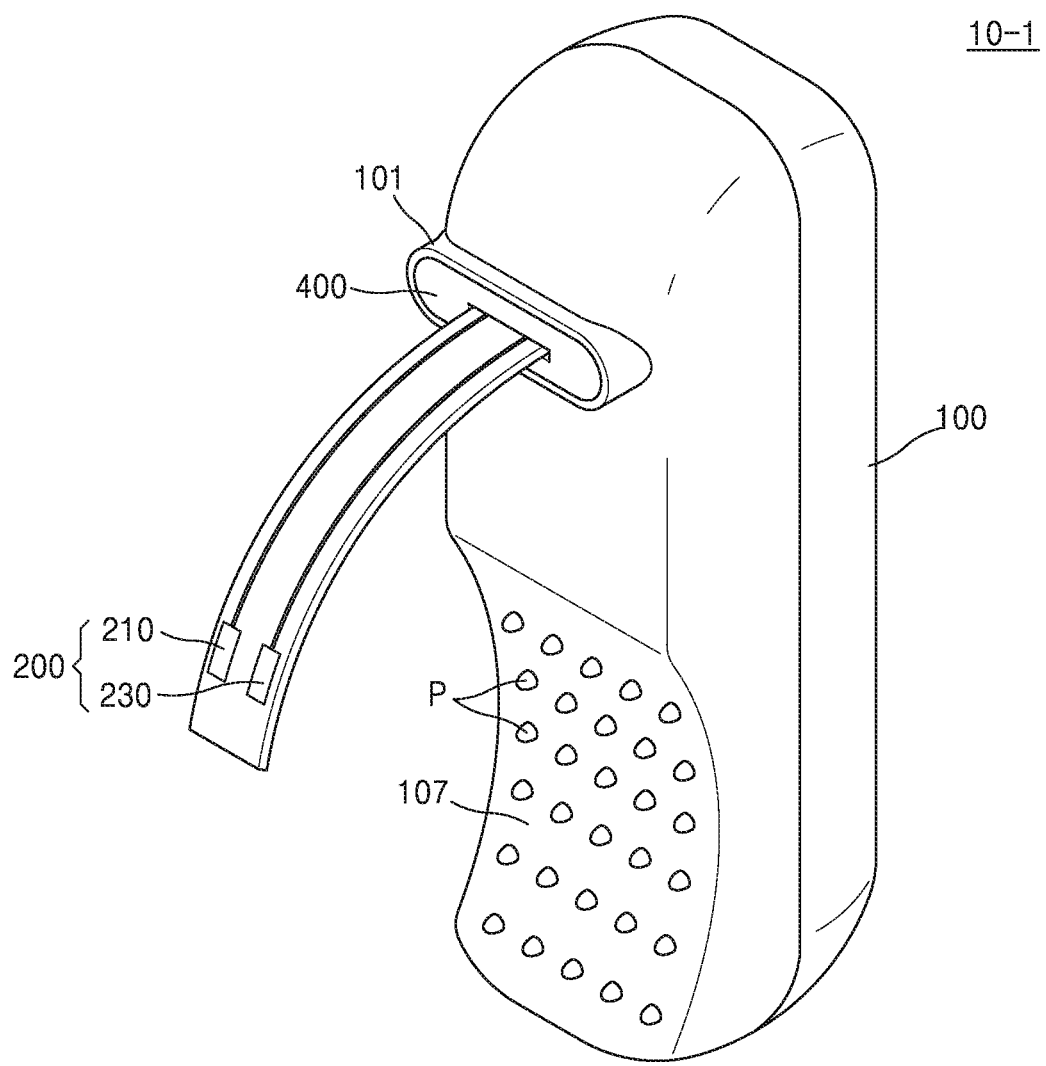
FIG. 5 is a conceptual view illustrating a pH measuring device according to another embodiment of the present disclosure.
Figure 6:
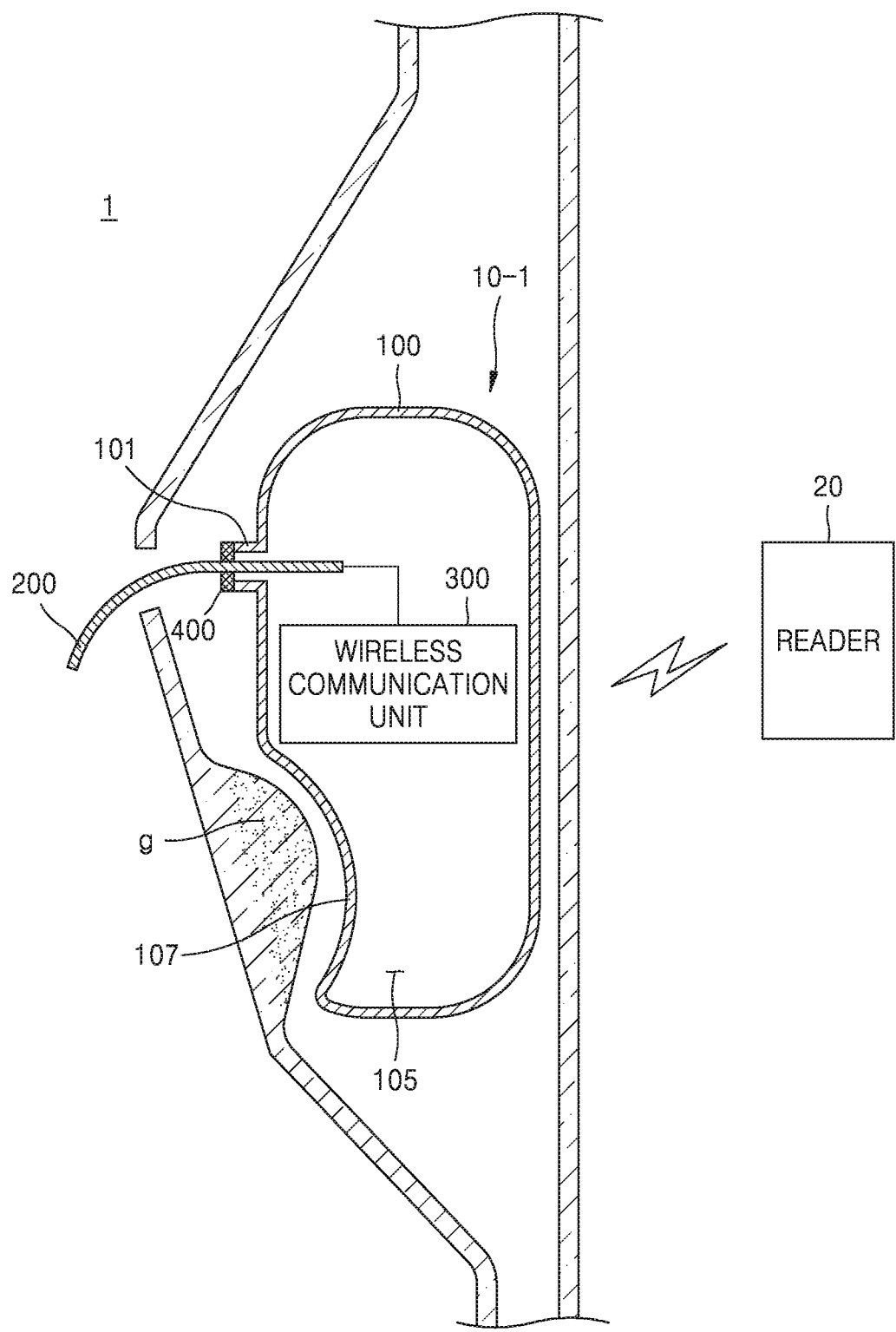
FIG. 6 is a view for describing a state in which the pH measuring device of FIG. 5 is inserted into a living body.

FIG. 5 is a conceptual view illustrating a pH measuring device 10-1 according to another embodiment of the present disclosure, and FIG. 6 is a view for describing a state where the pH measuring device 10-1 of FIG. 5 is inserted into a living body.

Referring to FIGS. 5 and 6, the pH measuring device 10-1 according to another embodiment of the present disclosure may include the body unit 100, the electrode unit 200, the wireless communication unit 300, and the sealing member 400. Elements of the pH measuring device 10-1 according to another embodiment are the same as those of the pH measuring device 10 of an embodiment except that a concave groove 107 is formed in the body unit 100, and thus a repeated explanation thereof will not be given.

The body unit 100 may include the hollow portion 105 therein, and may include the through-portion 101 formed in a first region so that the hollow portion 105 communicates with the outside. Corners of the body unit 100 may be round to minimize an examinee's discomfort when the body unit 100 is inserted into an esophageal wall. Also, the body unit 100 may be formed of a harmless material even when the body unit 100 is inserted into the living body. The through-portion 101 may be formed in the first region of the body unit 100, and the electrode unit 200 electrically connected to an internal circuit through the through-portion 101 may be exposed to the outside.

The concave groove 107 that is concave inward from a surface of the body unit 100 may be formed in a second region spaced apart by a predetermined interval from the first region of the body unit 100. As shown in FIG. 5, the pH measuring device 10 or 10-1 may be inserted into the esophageal wall to expose a part of the electrode unit 200 through an opening penetrating a part of the esophageal wall and measure the pH in the esophagus. In this case, in order to stably fix the pH measuring device 10-1, a polyp g may be artificially formed inside the esophageal wall. The concave groove 107 may be formed in the body unit 100 so that the polyp g is easily inserted into the concave groove 107. Although the concave groove 107 is formed in the same body surface as the through-portion 101 in FIG. 6, the present disclosure is not limited thereto. The concave groove 107 may be formed in a second surface opposite to a first surface in which the through-portion 101 is formed, or may be formed in both the first surface and the second surface.

A plurality of uneven portions P may be formed on an outer surface of the concave groove 107. Because the roughness of the outer surface of the concave groove is increased due to the uneven portions P, the concave groove 107 may be more stably fixed to the polyp g. Although the uneven portions P may protrude outward from the concave groove 107 as shown in FIG. 5, the present disclosure is not limited thereto and the uneven portions P may include a plurality of grooves concave inward from a surface of the body unit 100.

As described above, because the pH measuring device according to embodiments of the present disclosure transmits a pH measurement value wirelessly to the outside while being inserted into the esophagus, a user's pain may be minimized, a stable pH measurement value may be obtained, and thus the accuracy of diagnosing gastroesophageal reflux disease may be improved.

While the present disclosure has been particularly shown and described with reference to embodiments thereof, they are provided for the purposes of illustration and it will be understood by one of ordinary skill in the art that various modifications and equivalent other embodiments may be made from the present disclosure. Accordingly, the true technical scope of the present disclosure is defined by the technical spirit of the appended claims.

INDUSTRIAL APPLICABILITY

The present disclosure provides a pH measuring device. Also, embodiments of the present disclosure may be applied to an implantable pH monitoring system for industrial use.

The invention claimed is:

1. A pH measuring device comprising:
   a body unit comprising a hollow portion therein and a through-portion formed in a first region so that the hollow portion communicates with an environment;
   an electrode unit comprising a first end, a second end, a reference electrode and a sensing electrode comprising different materials and configured to sense a pH measurement value in a living body by allowing the first end to be located in the hollow portion and the second end opposite to the first end to be exposed to an outside of the body unit through the through-portion; and
   a wireless data transmitter configured to transmit the pH measurement value sensed by the electrode unit to a reader outside the pH measuring device,
   the body unit further comprising a concave groove that is formed to be concave toward an inside of the body unit so as to fix the body unit to an esophageal wall of an esophagus of the living body, wherein the concave groove is formed in a second region spaced apart from the first region and comprises a plurality of uneven portions formed on an outer surface of the concave groove,
   wherein the pH measuring device is configured to be inserted into the esophageal wall and seated on a submucosal tissue of the esophageal wall,
   wherein the concave groove is configured to be seated on a polyp formed on the inside of the esophageal wall,
   wherein the electrode unit is configured to be exposed into the esophagus through an opening penetrating the esophageal wall, and
   wherein the through-portion is configured to be disposed to face the opening.

2. The pH measuring device of claim 1, wherein the reference electrode is a silver/silver chloride (Ag/AgCl) electrode, and
   the sensing electrode is formed of at least one metal oxide selected from the group consisting of iridium/iridium oxide (Ir/IrOx), tin oxide ($SnO_2$), platinum oxide ($PtO_2$), titanium dioxide ($TiO_2$), osmium dioxide ($OsO_2$), rhodium dioxide ($RhO_2$), ruthenium oxide ($RuO_2$), and tantalum pentoxide ($Ta_2O_5$).

3. The pH measuring device of claim 1, wherein the wireless data transmitter is electrically connected to the electrode unit and is configured to transmit the sensed pH measurement value to the reader using a resonant circuit comprising an inductor and a capacitor.

4. The pH measuring device of claim 1, wherein the body unit is formed of at least one material selected from the group consisting of ceramic, polymer, and plastic.

5. A pH monitoring system comprising:
   a pH measuring device comprising:
      a body unit comprising a hollow portion therein and a through-portion formed in a first region so that the hollow portion communicates with a reader outside the pH measuring device,
      an electrode unit comprising a first end, a second end, a reference electrode and a sensing electrode comprising different materials and configured to sense a pH measurement value in a living body by allowing the first end of to be located in the hollow portion and the second end opposite to the first end to be exposed to an outside of the body unit through the through-portion, and
      a wireless data transmitter configured to transmit the pH measurement value sensed by the electrode unit to the reader; and the reader configured to receive the pH measurement value transmitted from the wireless data transmitter of the pH measuring device, the body unit further comprising a concave groove that is formed to be concave toward an inside of the body unit so as to fix the body unit to an esophageal wall of an esophagus of the living body, wherein the concave groove is formed in a second region spaced apart from the first region and comprises a plurality of uneven portions formed on an outer surface of the concave groove, wherein the pH measuring device is configured to be inserted into the esophageal wall and seated on a submucosal tissue of the esophageal wall, wherein the concave groove is configured to be seated on a polyp formed on the inside of the esophageal wall, wherein the electrode unit is configured to be exposed into the esophagus through an opening penetrating the esophageal wall, and wherein the through-portion is configured to be disposed to face the opening.

6. The pH monitoring system of claim 5, wherein the wireless data transmitter is electrically connected to the electrode unit and is configured to transmit the sensed pH measurement value to the reader through a resonant frequency by using a resonant circuit comprising an inductor and a capacitor.

7. The pH monitoring system of claim 5, wherein the reference electrode is a silver/silver chloride (Ag/AgCl) electrode, and the sensing electrode is formed of at least one metal oxide selected from the group consisting of iridium/iridium oxide (Ir/IrOx), tin oxide ($SnO_2$), platinum oxide ($PtO_2$), titanium dioxide ($TiO_2$), osmium dioxide ($OsO_2$), rhodium dioxide ($RhO_2$), ruthenium oxide ($RuO_2$), and tantalum pentoxide ($Ta_2O_5$).

8. A method of using a pH measuring device, the method comprising:
providing the H measuring device comprising:
a body unit comprising a hollow portion therein and a through-portion formed in a first region so that the hollow portion communicates with an environment,
an electrode unit comprising a first end, a second end, a reference electrode and a sensing electrode comprising different materials and configured to sense a pH measurement value in a living body by allowing the first end to be located in the hollow portion and the second end opposite to the first end to be exposed to an outside of the body unit through the through-portion,
a wireless data transmitter configured to transmit the pH measurement value sensed by the electrode unit to a reader outside the pH measuring device, and
the body unit further comprising a concave groove that is formed to be concave toward an inside of the body unit so as to fix the body unit to an esophageal wall of an esophagus of the living body, wherein the concave groove is formed in a second region spaced apart from the first region and comprises a plurality of uneven portions formed on an outer surface of the concave groove; and
inserting the pH measuring device into the esophageal wall such that:
the pH measuring device is seated on a submucosal tissue of the esophageal wall,
the concave groove is seated on a polyp formed on the inside of the esophageal wall,
the electrode unit is exposed into the esophagus through an opening penetrating the esophageal wall, and
the through-portion is disposed to face the opening.

* * * * *